(12) United States Patent
Jensen et al.

(10) Patent No.: US 6,387,353 B1
(45) Date of Patent: *May 14, 2002

(54) LIGHT OR HEAT ACTIVATED DENTAL BLEACHING COMPOSITIONS

(75) Inventors: Steven D. Jensen, Riverton; Dan E. Fischer, Sandy, both of UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/373,434

(22) Filed: Aug. 11, 1999

Related U.S. Application Data

(63) Continuation of application No. 09/010,155, filed on Jan. 21, 1998, which is a continuation-in-part of application No. 08/781,662, filed on Jan. 10, 1997, now Pat. No. 5,785,527.

(51) Int. Cl.⁷ .................................................. A61K 7/16
(52) U.S. Cl. ......................... 424/49; 424/533; 433/215
(58) Field of Search ............................ 424/49, 53, 613, 424/616; 252/186.38, 186.41; 433/29, 215

(56) References Cited

U.S. PATENT DOCUMENTS

| | | | |
|---|---|---|---|
| 3,499,844 A | | 3/1970 | Kibbel et al. ................ 252/316 |
| 3,949,477 A | | 4/1976 | Cohen et al. ................ 32/14 A |
| 4,385,344 A | | 5/1983 | Gonser ........................ 362/32 |
| 4,450,139 A | | 5/1984 | Bussiere et al. .......... 422/186.3 |
| 4,839,157 A | | 6/1989 | Mei-King et al. ............. 424/53 |
| 4,867,988 A | | 9/1989 | Chernack .................... 424/490 |
| 4,952,143 A | | 8/1990 | Becker et al. ................. 433/32 |
| 4,976,955 A | | 12/1990 | Libin .......................... 424/53 |
| 5,000,941 A | | 3/1991 | Chernack .................... 424/490 |
| 5,015,408 A | | 5/1991 | Reuss .......................... 252/99 |
| 5,032,178 A | * | 7/1991 | Corneil ........................ 106/35 |
| 5,217,710 A | | 6/1993 | Williams et al. ............. 424/52 |
| 5,256,402 A | * | 10/1993 | Prencipe et al. .............. 424/53 |
| 5,279,816 A | | 1/1994 | Church et al. ................ 424/53 |
| 5,290,169 A | | 3/1994 | Friedman et al. ............. 433/29 |
| 5,302,375 A | | 4/1994 | Viscio ......................... 424/53 |
| 5,312,249 A | | 5/1994 | Kennedy .................... 433/29 |
| 5,316,473 A | | 5/1994 | Hare ........................... 433/29 |
| 5,371,826 A | | 12/1994 | Friedman .................... 385/115 |
| 5,372,802 A | | 12/1994 | Barrow et al. ............... 424/52 |
| 5,372,826 A | | 12/1994 | Friedman .................... 385/115 |
| 5,425,953 A | * | 6/1995 | Sintov et al. ................ 424/404 |
| 5,487,662 A | | 1/1996 | Kipke et al. ................. 433/37 |
| 5,645,428 A | | 7/1997 | Yarborough ................. 433/215 |
| 5,683,679 A | * | 11/1997 | Sharma ....................... 424/53 |
| 5,713,738 A | * | 2/1998 | Yarborough ................. 433/215 |
| 5,766,011 A | * | 6/1998 | Sibner ........................ 433/215 |
| 5,785,527 A | * | 7/1998 | Jensen et al. ................ 433/215 |
| 5,813,854 A | | 9/1998 | Nikodem .................... 433/29 |
| 5,858,332 A | * | 1/1999 | Jensen et al. ................ 424/53 |
| 6,106,293 A | | 8/2000 | Wiesel ........................ 433/215 |

FOREIGN PATENT DOCUMENTS

EP 0 105 747 * 4/1984

OTHER PUBLICATIONS

English translation of Kotkowski. Roczniki PZH 19(1)69–78, 1968.*

Kotkowski S. Some Physico–Chemical Properties of Food Dyes. Pocz Panstw Zakl Hig 19(1)69–68, Jan. 1968.*

Thompson K. J Chem Soc Faraday Trans. 89(22)4035–4043, 1993.*

Howard E. Strassler et al. *Whitening. Note the grand scale of bleaching.* RDH 17 (6) 24–28,30 No Date Avail.

Optilux 400/401 Curing Light and Light Guides; *Ultradent Materials & Procedures Manual,* p. 115, 1996.

Thompson K. Mechanism of Peroxide Bleaching at High pH. J Chem Soc (21)1600–1, 1992.*

Thompson K. Mechanism of Bleaching by Peroxides. J Chem Soc Faraday Trans 89(22)4035–4043, 1993.*

Optilux® 400/401 Curing Light and Light Guides; *Ultradent Materials & Procedures Manual,* p. 115, 1996.

* cited by examiner

Primary Examiner—Ralph Gitomer
(74) Attorney, Agent, or Firm—Workman, Nydegger, Seeley

(57) ABSTRACT

Dental bleaching compositions are made with a bleaching agent and a stable radiant-energy absorbing compound that acts as a bleaching agent activator. The dental bleaching compositions of the present invention can be one-part, pre-mixed compositions that do not require mixing at the time of treating a patient's teeth but which remain stable over time. The bleaching agent may consist of hydrogen peroxide, either in aqueous form or complexed with urea (carbamide peroxide) or sodium perborate. The bleaching agent activator includes hydrocarbons that are stable in the presence of the bleaching agent, which do not prematurely accelerate liberation of the bleaching agent, but which allow for selective activation of the bleaching agent by irradiation of the bleaching composition with radiant energy. The bleaching composition may optionally include a neutralizing agent to adjust the pH, a carrier to help provide proper consistency and potency, and a stabilizing agent to maintain maximum potency of the bleaching agent over time. The bleaching composition may also include a thickening agent to achieve a selected viscosity. The dental bleaching compositions may be adapted to be loaded into and delivered from a syringe.

25 Claims, No Drawings

LIGHT OR HEAT ACTIVATED DENTAL BLEACHING COMPOSITIONS

RELATED APPLICATIONS

This application is a continuation of copending U.S. application Ser. No. 09/010,155, filed Jan. 21, 1998, which is a continuation-in-part of U.S. application Ser. No. 08/781,662, filed Jan. 10, 1997, now U.S. Pat. No. 5,785,527. For purposes of disclosure, the foregoing applications and patent are incorporated herein by specific reference.

BACKGROUND OF THE INVENTION

1. The Field of the Invention

The present invention relates to dental bleaching compositions and methods for treating tooth surfaces. More particularly, the present invention is directed to a stable one-component viscous/gelled dental bleaching composition that has a high concentration of bleaching agent. The dental bleaching compositions of the present invention include a radiant-energy or heat-energy absorbing substance that causes the bleaching agent to more quickly bleach the tooth surfaces.

2. The Relevant Technology

The use of certain foods and tobacco, the process of aging, diseases, trauma, medications, some congenital conditions, and environmental effects can cause teeth to become discolored. Because white or whitened teeth are usually considered to be aesthetically superior to stained or discolored teeth, there has been a heightened level of interest of late in developing compositions and methods for bleaching teeth.

A tooth is comprised of an inner dentin layer and an outer hard enamel layer that is slightly porous. The outer layer is the protective layer of the tooth. The natural color of the tooth is opaque to translucent white or slightly off-white.

Some dentrifices, like toothpastes, gels, and powders, contain active oxygen or hydrogen peroxide liberating bleaching agents. Such bleaching agents include peroxides, percarbonates and perborates of the alkali and alkaline earth metals or complex compounds containing hydrogen peroxide. Also, peroxide salts of the alkali or alkaline earth metals are known to be useful in whitening teeth.

The most commonly used dental bleaching agent is carbamide peroxide ($CO(NH_2)_2 \cdot H_2O_2$), also called urea hydrogen peroxide, hydrogen peroxide carbamide, and perhydrolurea. Carbamide peroxide has been used by dental clinicians for several decades as an oral antiseptic. Tooth bleaching was an observed side effect of extended contact time. Over-the-counter compositions of 10% carbamide peroxide are available as "GLYOXIDES®" by Marion Laboratories and "PROXIGEL®" by Reed and Carnrick. An extended-contact application of bleaching gel held in a dental tray is available as "OPALESCENCE®" by Ultradent. Other bleaching agents such as peroxyacetic acid ($CH_3C=OO-OH$) and sodium perborate, are also known in the medical, dental and cosmetic arts.

Patients who have desired to have their teeth whitened have typically done so by applying a bleaching composition to the teeth by means of the dental tray for repeated treatments, or they had to submit to conventional in-office bleaching techniques that required from 4 to 10 visits to the dental office before clinically significant results were achieved. Less effective teeth whitening was also done by the use of toothpastes or polishes that were applied by brushing. Clinically significant results are quantifiable such as by measuring gray scale, L*, and as to yellowness or blueness, b*, in the CIE® system of color measurement or by equivalent methods.

Bleaching compositions have been manufactured in one-part and two-part systems. A one-part system consists of a compound in which the active bleachant is dispersed into inert components to form an emulsion or gel. One-part systems can also further consist of mixtures in which stabilizers are used to prevent premature decomposition of the peroxide in the bleaching composition. The advantage of a one-part system is ease of use and convenience. The main disadvantage is that prior art one-part bleaching compositions generally contain relatively low concentrations of peroxide due to the instability of more highly concentrated peroxide compositions. Thus, current one-part systems have a low potency and are slow to react. Most one-part systems in the past have included active peroxide in a range of up to about 3.5% by weight. Due to the relatively low concentration of active bleaching agent in one-part systems, about 10 applications on average are necessary for effective bleaching.

In a two-part system, aqueous hydrogen peroxide is mixed with other components to achieve a preferred higher viscosity. These components are mixed just prior to bleaching due to the incompatibility of the other components with hydrogen peroxide. The main advantage of a two-part system is that it allows for much higher concentrations of active peroxide that cannot exist stably as a one-part system for incidental off-the-shelf use. This results in faster bleaching of the patient's teeth due to the higher peroxide concentration. Faster bleaching is desirable, especially where patient compliance with longer bleaching regimens is problematic, or if only one or a few teeth need bleaching.

Another example of a two-part system is microencapsulation of the bleaching agent and a stabilizer. The microcapsules would separate the bleaching agent from the carrier and other materials and would rupture only upon physical shear caused by a tooth brush. The dental bleaching effect of the microencapsulation system is only visible after prolonged use due to its low peroxide concentration or low activation rate.

Although positive results using the foregoing techniques have been reported, the effectiveness of the techniques depends upon such factors as type and intensity of the stain, bleaching agent contact time on the teeth, the amount of available active bleachant in the bleaching agent, and the persistence of the individual in applying the treatment until the desired result is accomplished.

Notwithstanding the foregoing advantages, there remain some important disadvantages to current one-part and two-part systems. A disadvantage to the two-part system is that the bleaching composition must be mixed on-site in the operatory immediately before application to the patient's tooth. Mixing requires additional time by the dental professional, which lowers efficiency and represents an extra preparatory procedure. Mixing in proper amounts is also important in order to yield consistent results.

Another disadvantage with two-part bleaching compositions is that, once mixed, the bleaching compositions must be used soon, since they are unstable and tend to decompose through the release of oxygen from the peroxide moieties. Often, the constituents of the bleaching compositions themselves accelerate decomposition rates. While such accelerants are useful in promoting faster bleaching, they yield a composition having a very short lifespan. Because known accelerants are chemical in nature, they cannot be added until bleaching is to commence. Otherwise the premature release of active oxygen will quickly decrease the potency of the bleaching composition. Moreover some accelerant(s) or peroxide indicators are unstable in that they themselves are consumed by the peroxide. The tendency of prior art accelerants or indicators to be themselves consumed has the effect of reducing the concentration of both the peroxide and the accelerant over a short period of time, thus reducing the effectiveness of each.

From the foregoing, it will be appreciated that what is needed in the art are stable, one-part, pre-mixed viscous/gelled bleaching compositions and methods for treating tooth surfaces that allow for greatly increased bleaching rates compared to existing one-part systems.

Additionally, it would be a significant advancement in the art to provide stable, one-part, pre-mixed viscous/gelled dental bleaching compositions for treating tooth surfaces that included means for accelerating the release of active oxygen from the bleaching agent when needed but which do not cause premature decomposition of the active dental bleaching agent or destruction of the bleaching agent activator.

It would still be a further advancement in the art to provide stable, one-part, pre-mixed viscous/gelled dental bleaching compositions that included higher concentrations of bleaching agent compared to existing one-part compositions that are made at the time of manufacture.

It would be a further advancement in the art to provide ingredients that more efficiently convert radiant energy to heat to obviate the need for prior art light sources that are clumsy or uncomfortable in the operatory or are slow in causing the release of active oxygen.

Such stable, one-part, pre-mixed dental bleaching compositions and methods for bleaching tooth surfaces are disclosed and claimed herein.

SUMMARY AND OBJECTS OF THE INVENTION

The present invention comprises stable, one-part, pre-mixed dental bleaching compositions made with a bleaching agent and a radiant-energy absorbing constituent that acts as a bleaching agent activator. The dental bleaching compositions of the present invention are one-part, pre-mixed compositions with a sufficient shelf life to allow for storage in the operatory of a dental professional for use when needed. Preferred bleaching agents include peroxides such as hydrogen peroxide and carbamide peroxide (which is a complex between urea and hydrogen peroxide). Preferred bleaching agent activators include radiant-energy absorbing substances, preferably substantially conjugated hydrocarbons such as aromatic rings or conjugated chains, that are stable in the presence of the bleaching agent in varying concentrations and that will not cause premature decomposition of the bleaching agent before the composition has been irradiated with radiant energy.

A thickening agent can be used to give the dental bleaching composition a desired consistency, thickness, and viscosity. Preferred thickening agents include PEMULEN®, a proprietary compound from B. F. Goodrich, or a compositional or chemical equivalent thereof.

An important advantage of the preferred bleaching compositions of the present invention are that they are stable over time. A major cause of premature degradation of the bleaching agent is the existence of errant or residual metal ions that can act as bleaching agent catalysts. Hence, it is possible to create stable bleaching compositions even at high concentrations (greater than 20% by weight) by avoiding, removing, or trapping errant or residual metal ions.

Scavenging of errant or residual metal ions can be accomplished by means of a bleaching agent stabilizer. The bleaching agent stabilizer comprises edetate disodium, EDTA, oxine EDTA, calcium disodium EDTA, adipic acid, succinic acid, citric acid, tin nitrates, tin phosphates, their respective salts, their combinations, and the like.

Activation of the dental bleaching composition of the present invention is accomplished with a bleaching agent activator that is preferably a radiant-energy or heat-energy absorbing substance. Examples of such substances include radiant-energy absorbing, substantially conjugated hydrocarbons such as aromatic hydrocarbons, multiple double-bond hydrocarbon chains, chain-aromatic mixtures, reacted combinations thereof, and equivalents. Specific examples include caroteneoids such as bixin, lycoxanthin, lycophil, canthaxanthin, capsanthin, cryptoxanthin, isomers of carotene, and lycopene. Other specific examples include aromatics such as coronene, fluoranthene, naphtho[2,3-a]pyrene, trans-4,4'-diphenylstilbene, 9,10-diphenylanthracene, 5,12-bis (phenyethynyl) napthacene, 9,10-bis (phenylethynyl) anthracene, and perylene. The foregoing compounds may optionally include one or more carboxyl groups. The only limitations are (1) that the radiant-energy absorbing substance does not cause substantial peroxide decomposition over time, and (2) that the radiant-energy absorbing substance be substantially peroxide resistant in the presence of the bleaching agent over time. Preferred bleaching agent activators include 9,10-bis (phenylethynyl) anthracene, perylene, and isomers of carotene and carboxyl-substituted variations thereof.

The bleaching compositions preferably include an inert or non-problematic carrier. The carrier may include, but is not limited to water, polypropylene glycol, polyethylene glycol, sorbitol, propylene glycol, glycerol, steryl alcohol, large molecular weight polyols, mixtures of the foregoing, and equivalents.

Because the bleaching compositions of the present invention are both stable in a one-part, pre-mixed system and include the radiant-energy absorbing substance, the bleaching process is greatly simplified. The dental bleaching compositions may advantageously be either preloaded or loaded manually into and dispensed from a syringe onto the patient's teeth. The dental professional simply places a desired quantity of the dental bleaching composition on the patient's teeth and then triggers accelerated bleaching by either irradiating the bleaching composition with radiant energy, such as visible and/or UV light, or by applying e.g. conductive heat energy to the composition before, during, or after application to the teeth. Depending on the desired rate of bleaching and patient sensitivity to bleaching agents, a bleaching composition having the optimum amount of bleaching agent can be selected before bleaching commences or can be determined by noting the results of the first bleaching treatment.

In view of the foregoing, it is an object of the present invention to provide stable, one-part, pre-mixed viscous/gelled bleaching compositions and methods for treating tooth surfaces that allow for greatly increased bleaching rates compared to existing one-part systems.

It is a further object and feature of the present invention to provide stable, one-part, pre-mixed viscous/gelled dental bleaching compositions for treating tooth surfaces that include means for accelerating the release of active oxygen from the bleaching agent when needed but which does not cause premature decomposition of the active dental bleaching agent or destruction of the bleaching agent activator.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The one-part, pre-mixed dental viscous/gelled bleaching compositions of the present invention are comprised of several components that, working in concert, provide a stable and effective viscous/gelled one-part, pre-mixed dental bleaching composition. The inventive bleaching compositions are stable over time but can be caused to accelerate bleaching by means of radiant or heat energy. The components include a bleaching agent, a thickening agent or gelling agent, a neutralizing agent, a carrier, a bleaching agent stabilizer, and a bleaching agent activator. Each component contributes to the dental bleaching composition in different ways.

A. Bleaching Agents

Preferred bleaching agents include hydrogen peroxide and hydrogen peroxide-containing complexes, such as carbamide peroxide $(NH_2)_2CO.H_2O_2$. Peroxides can provide a ready source of active oxygen in effective concentrations.

Hydrogen peroxide is the preferred bleaching agent in some cases, especially where it is desired to include a relatively high concentration of bleaching agent concentrations. Because of the nature of hydrogen peroxide, it is only available as an aqueous solution. Aqueous hydrogen peroxide solutions from 3% to 90% by weight hydrogen peroxide are commercially available.

On the other hand, carbamide peroxide can provide a nonaqueous form of available hydrogen peroxide. Carbamide peroxide in its pure form is a crystalline substance consisting of a molecule of urea complexed with a single molecule of hydrogen peroxide. Carbamide peroxide is generally more stable than aqueous hydrogen peroxide and is often preferred for that reason. However, because of the existence of the urea molecule, pure crystalline urea peroxide contains only about 36% available hydrogen peroxide. This means that the upper limit of available peroxide for bleaching when only using carbamide peroxide is lower than 36% when significant quantities of other components such as water, proplyene glycol, or glycerol and the like are included in the bleaching composition.

The type and amount of hydrogen peroxide to be used will depend on the desired peroxide concentration in the final dental bleaching composition. In general, it will be preferable to use concentrated hydrogen peroxide solutions when it is desired to manufacture a bleaching composition having high concentrations of bleaching agent. Lower concentrated hydrogen peroxide solutions and/or carbamide peroxide and/or sodium perborate are generally used when it is desired to manufacture a bleaching composition having lower concentrations of bleaching agent. Carbamide peroxide solutions and hydrogen peroxide solutions can be mixed together in varying concentrations to yield bleaching compositions having a wide spectrum of bleaching agent concentrations. Additionally, sodium perborate can be used alone or it can be mixed with each or both of hydrogen peroxide and carbamide peroxide.

Because hydrogen peroxide is generally less stable with increasing pH, many hydrogen peroxide solutions include acidifying agents such as mineral acids in order to render a more stable hydrogen peroxide solution. However, upon mixing such solutions with the other constituents to yield the dental composition of the present invention, it will generally be desired to adjust the pH to an acceptable pH range in order to protect the patient's teeth and surrounding tissues. The concept of pH adjustment will be discussed herein below.

B. Thickening agents

Thickening agents or gelling agents assist to increase viscosity, to facilitate ease of placement, and to assure the composition stays in place during treatment. Thus, thickening agents aid the composition to remain in place during treatment. Thickening agents preferably have the quality of being substantially inert in the presence of, and not readily decomposed by, the bleaching agent. It has been found that thickening agents that are substantially hydrophilic but have a relatively small lipophilic moiety, are preferred in the present invention. For example, a preferred thickening agent is an emulsifier comprising a high molecular weight polyacrylic acid polymer or copolymer.

As an example of a preferred thickening agent, we have found that PEMULEN® or a compositional or chemical equivalent thereof possesses the qualities required for the inventive composition. A more preferred thickening agent is PEMULEN® TR-1NF. PEMULEN® is a propriety formula that includes a significant quantity of a polyacrylic copolymer that has a slightly hydrophobic end and a strongly hydrophilic end.

In addition to PEMULEN® or a compositional or chemical equivalent thereof, we have found that silicates may be used; however, the composition loses its gell like qualities that are preferred during application. When such gell-like qualities are lost, the composition becomes too stiff to extrude through e.g. a syringe orifice that can otherwise be used to extrude compositions of the present invention.

We have also found that the composition of the present invention can be used with hydrogen peroxide concentrations well below 20%, and in which the thickening agent is present in quantities sufficient to make the composition a thick, sticky, and viscous gell. Such hydrogen peroxide concentrations can be as low as 0.1%.

C. Neutralizing Agents

In light of the acidity of hydrogen peroxide stock solutions and some solutions of polyacrylic acid thickeners such as PEMULEN or a compositional or chemical equivalent thereof, it is usually desired to use a neutralizing agent to adjust the pH to within an acceptable pH range. Raising the pH causes some thickeners to become more viscous. In addition, bleaching compositions that are too acidic can etch the patient's teeth and cause irritation to surrounding dental tissues. In most cases, the pH will be in a range from about 2 to about 9, more preferably in a range from about 3 to about 7, and most preferably from about 4 to about 6. Preferred neutralizing agents include alkali hydroxides, such as sodium hydroxide and potassium hydroxide, amines such as diisopropanol amine and triethanol amine, ammonium hydroxide, and the like. The most preferred neutralizing agent is sodium hydroxide, 50 percent in distilled or deionized water.

D. Carriers

The carrier is used to complement the other dental bleaching composition components and effect good dispersion and stability of the resulting compositions. By adjusting the amount of carrier the bleaching agent concentration can be adjusted to a selected level. The use of a carrier or carrier combinations aligned with a thickening agent allows for achievement of a selected bleaching agent concentration and a selected consistency. Water, or water in combination with other components including other carriers is sometimes used. Other carriers include polyols, such as polypropylene glycol, polyethylene glycol, sorbitol, propylene glycol, glycerol, ethylene glycol, large molecular weight polyols, and the like, and mixtures of the above. Although ethylene glycol could work as a carrier, it is not used because it is toxic. The carrier may comprise stearyl alcohol.

E. Bleaching Agent Stabilizers

The bleaching agent stabilizers act as impurity scavengers that bind with errant or residual metal ions and other impurity elements that might cause decomposition of the bleaching agent. The stabilizer also must not itself be a source of bleaching agent instability. Where an excess of stabilizer is in solution such that all impurities have been bound up by the stabilizer, the excess stabilizer must itself be inert to the bleaching agent. At least two classes of bleaching agent stabilizers are part of the present invention. One class comprises carboxylic acid chelators, such as edetate disodium, EDTA, oxine EDTA, calcium disodium EDTA, adipic acid, succinic acid, citric acid, and the like and mixtures thereof, their respective salts or derivatives. Another class of bleaching agent stabilizers consists of tin-containing salts, such as tin nitrates, tin phosphates, and the like.

F. Bleaching Agent Activators

Several bleaching agent activators are disclosed in the present invention such as radiant or thermal energy absorbable bleaching agent activators. The preferred qualities of bleaching agent activators include inertness to the bleaching agent and the ability to absorb energy and heat up, thus activating the bleaching agent.

Inert particles that act as a heat sink may also be used. These particles may absorb radiant or conducted thermal energy in such a way so as to not substantially chemically react with the peroxide during application. Such particles may include metals coated with inert films or metal-filled plastic resins.

It has been found that radiant-energy absorbable, substantially conjugated hydrocarbons are the preferred bleaching agent activators since they appear to be significantly stable in the presence of peroxides. In other words, they themselves resist oxidation or bleaching in the presence of the bleaching agent.

Preferred bleaching agent activators are defined as substantially conjugated hydrocarbons such as multiple benzene structures, conjugated hydrocarbon chains, and combinations thereof that absorb portions of the electromagnetic spectrum and that have simple hydrogen, hydroxyl, or carboxylic groups attached to the structures and that act as energy-absorbing substances.

The preferred multiple benzene structures can be as simple as naptha-based structures or anthracene-based structures. Useful substantially conjugated hydrocarbons that are benzene structures that are radiant energy absorbing include 9,10-bis(phenylethynyl)-anthracene, perylene, naphtho[2,3-a]pyrene, trans-4,4'-diphenylstilbene, 9,10-diphenylanthracene, 5,12-bis(phenyethynyl)-napthacene, coronene, fluoranthene, and equivalents.

The known substantially conjugated bond hydrocarbon chains include caroteneoids, such as bixin, lycoxanthin, lycophil, canthaxanthin, capsanthin, cryptoxanthin, isomers of carotene, and lycopene. Of the known substantially conjugated hydrocarbons, 9,10-bis (phenylethynyl)-anthracene, perylene, and isomers of carotene are preferred. Of the known substantially conjugated hydrocarbons, carboxyl-substituted hydrocarbons are also preferred.

Less preferred aromatic compositions such as 7-diethylamino 4-methyl coumarin, henna, and alizarin are less stable compared to the above-defined substantially conjugated hydrocarbons. Henna, a red dye known for at least 4,000 years, is a double-ketonated naphtha hydroxide. Alizarin, a red dye, is a double-ketonated anthracene meta double hydroxide. Although 7-diethylamino 4-methyl coumarin, henna, and alizarin are less preferred, to the extent that one were to use these substances within a stable, one-part, pre-mixed bleaching composition, such a composition would certainly be within the scope of the present invention.

Other substantially conjugated hydrocarbon structures that resist oxidation by peroxides are within the skill of the routineer in the art to find during routine experimentation after consultation with the present invention disclosure or by practicing the invention.

The bleaching agent activators in the dental bleaching composition of the present invention will preferably not only efficiently absorb radiant energy but also preferably will not significantly contribute to bleaching agent decomposition while the composition sits on the shelf. In this way, the inventive bleaching composition will have substantially the same shelf life as a bleaching composition that does not include the bleaching agent activator when stored at an appropriate temperature, e.g. 4° C. In addition to on-the-shelf inertness, it is also preferable that upon application of radiant energy, the bleaching agent activator itself does not substantially react with the oxidizer. The effect of a bleaching agent activator that resists oxidation during patient treatment is an increase in available activator relative to the remaining unreacted bleaching agent.

As radiant energy is applied to the dental bleaching composition, the bleaching agent activator begins to heat up and to accelerate the release of active oxygen from the bleaching agent.

Additionally, the bleaching agent activators of the present invention, particularly the preferred bleaching agent activators, could be used as colorants in hydrogen peroxide compositions such as dentifrices. Due to the stable quality of the preferred bleaching agent activators, they could be used a colorants for aesthetic reasons in otherwise uncolored hydrogen peroxide compositions.

G. General Properties

To make the dental bleaching composition of the present invention a viable off-the-shelf product for dental professionals, hydrogen peroxide decomposition must be minimized during storage. Because hydrogen peroxide decomposition is accelerated by increasing the temperatures, it is appropriate to store the inventive dental bleaching composition within an appropriate temperature range. e.g. about 4° C. A preferred shelf life is at least about one month, where the amount of available bleaching agent is at least about 95% of the original concentration. For about two months, it is preferable for there to remain at least about 90% of the original available bleaching agent. For about three months, it is preferable for there to remain at least about 80% of the original available bleaching agent.

Obviously, it will generally always be preferable to have more stable systems in which most, if not all, of the bleaching agent remains active over the length of the shelf life. It has been observed that dental bleaching compositions of the present invention remained substantially undecomposed for about three months. For example, samples of the inventive dental bleaching composition were stored refrigerated for 92 days and there remained about 99% of the original available hydrogen peroxide. Samples of the inventive dental bleaching composition were stored refrigerated for 127 days and there remained above 98% of the original available hydrogen peroxide. Additionally, samples of the inventive dental bleaching composition were stored unrefrigerated for 92 days and there remained about 95% of the original available hydrogen peroxide. Because periodic testing of available hydrogen peroxide revealed slow decomposition of the bleaching agent after about three months, it is within the contemplation of the present invention that if refrigerated, uncontaminated, and light-shielded, the inventive dental bleaching composition will contain about 50%, preferably about 90%, and most preferably about 95% of the original available hydrogen peroxide for about one year.

Stability of a dental bleaching composition with about 35% available hydrogen peroxide, wherein the dental bleaching agent maintains at least about 85% of its original strength about one month after manufacture, is understood to be a composition that would contain about 30% available hydrogen peroxide.

The dental bleaching compositions of the present invention can be made such that they include from about 0.1% to about 90% available hydrogen peroxide; from about 0.05% to about 5% thickening agent; from about 0% to about 10% neutralizing agent; from about 5% to about 80% carrier; from about 0.01% to about 5% stabilizer; and from about 0.001% to about 3% bleaching agent activator.

More preferred dental bleaching compositions of the present invention can be made such that they include from about 10% to about 80% available hydrogen peroxide; from about 0.5% to about 4% thickening agent; from about 0.5% to about 5% neutralizing agent; from about 10% to about 75% carrier; from about 0.1% to about 3% stabilizer; and from about 0.02% to about 2% bleaching agent activator.

Most preferred dental bleaching compositions of the present invention can be made such that they include from about 20% to about 60% available hydrogen peroxide; from about 1% to about 3% thickening agent; from about 0.6% to about 3% neutralizing agent; from about 15% to about 65% carrier; from about 0.5% to about 2% stabilizer; and from about 0.05% to about 1% bleaching agent activator.

H. Methods of Use

In light of the foregoing inventive features of the dental compositions of the present invention, the method for bleaching teeth is performed in the dental operatory under ordinary conditions. The dental professional applies a layer of the inventive dental bleaching composition on the labial surfaces of as many of the teeth as are desired to be bleached.

Thereafter, rapid bleaching is carried out by irradiating the teeth with radiant energy, such as visible and/or UV radiant energy, to accelerate decomposition of the bleaching agent. The radiant energy excites the dental bleaching activator, which causes the molecular bonds within the activator to vibrate vigorously and heat up the composition. The heated composition causes the accelerated release of free radical oxygen from the dental bleaching agent. The rate of heating can be controlled by the amount of light that is used.

The dental bleaching compositions may advantageously be loaded into and dispensed from a syringe onto the patient's teeth.

I. Examples of the Preferred Embodiments

In order to more fully teach the present invention, the following examples are presented. The examples are intended to be illustrative only and are certainly not intended to imply that other embodiments not specified are not within the scope of the present invention. Bleaching compositions were prepared according to the present invention and included the components and amounts set forth as Examples 1–28, which are set forth below Table 1.

In order to illustrate one exemplary manner of mixing together the components, attention is turned to Example 4, in which 254 g of propylene glycol was placed in a container and mixed with 12 g of PEMULEN® TR-1NF until homogenous. Next, stabilizers comprising 8 g each of edetate disodium and citric acid were mixed with water and added as stabilizers to the glycol-PEMULEN mixture to scavenge errant or residual metal ions. Thereafter, 4 g of beta carotene was added as the bleaching agent activator. Following addition of the bleaching agent activator, 705 g of 50% aqueous hydrogen peroxide was added. To the mixture was added 9 g of sodium hydroxide, 50% in water, and the resulting mixture was stirred until homogeneous. The other examples were mixed together in similar fashion, although the concentrations and identities of the components were altered in order to form the compositions as achieved.

Table 1 represents 28 exemplary compositions that were prepared according to the present invention and identified as Examples 1–28. In each sample, the bleaching agent was added in the form of aqueous hydrogen peroxide; therefore the number under the heading "$H_2O_2$" represents the net amount of hydrogen peroxide in the composition. Thus, the balance of the aqueous hydrogen peroxide was water. The thickener was PEMULEN® TR-1NF unless otherwise noted. The neutralizing agent was sodium hydroxide in 50% water. Other components are noted at the foot of Table 1.

TABLE 1

| Example | Active $H_2O_2$ | Water | Thickener | NaOH | Carrier | Stabilizer | Activator | Total |
|---|---|---|---|---|---|---|---|---|
| 1 | 30.25 | 30.25 | 1.2 | 0.9 | 36.4[1] | 1.0[2] | — | 100.0 |
| 2 | 30.5 | 30.5 | 1.5 | 0.8 | 36.7[3] | — | — | 100.0 |
| 3 | 30.5 | 30.5 | 1.2 | 0.9 | 36.9[4] | — | — | 100.0 |
| 4 | 35.25 | 35.25 | 1.2 | 0.9 | 25.4[1] | 1.6[5] | 0.4[6] | 100.0 |
| 5 | 35.25 | 35.25 | 1.2 | 0.9 | 27.4[3] | — | — | 100.0 |
| 6 | 35.25 | 35.25 | 1.2 | 0.9 | 27.4[4] | — | — | 100.0 |
| 7 | 35.25 | 35.25 | 1.2 | 0.9 | 27.4[6] | — | — | 100.0 |
| 8 | 35.25 | 35.25 | 1.2 | 0.9 | 27.3[3] | 1.0[2] | — | 100.0 |
| 9 | 35.25 | 35.25 | 1.2 | 0.9 | 27.2[3] | 0.2[2] | — | 100.0 |
| 10 | 35.25 | 35.25 | 1.2 | 0.9 | 26.4[1] | 1.0[2] | — | 100.0 |
| 11 | 35.25 | 35.25 | 1.2 | 0.9 | 26.4[4] | 1.0[2] | — | 100.0 |
| 12 | 35.25 | 35.25 | 1.2 | 0.9 | 26.0[1] | 1.0 | 0.4[7] | 100.0 |

TABLE 1-continued

| Example | Active H$_2$O$_2$ | Water | Thickener | NaOH | Carrier | Stabilizer | Activator | Total |
|---|---|---|---|---|---|---|---|---|
| 13 | 35.25 | 35.25 | 1.2 | 0.9 | 26.0[1] | 1.4[8] | — | 100.0 |
| 14 | 35.25 | 35.25 | 1.2 | 0.9 | 25.9[1] | 1.5[9] | — | 100.0 |
| 15 | 35.25 | 35.25 | 1.2 | 0.9 | 25.5[1] | 1.5[9] | 0.4[10] | 100.0 |
| 16 | 35.25 | 35.25 | 1.2 | 0.9 | 25.8[1] | 1.5[9] | 0.1[10] | 100.0 |
| 17 | 35.25 | 35.25 | 1.2 | 0.9 | 25.5[1] | 1.8[11] | 0.1[10] | 100.0 |
| 18 | 35.25 | 35.25 | 1.2 | 0.9 | 25.7[1] | 1.6[12] | 0.1[10] | 100.0 |
| 19 | 35.25 | 35.25 | 1.2 | 0.9 | 25.7[1] | 1.8[13] | 0.1[10] | 100.0 |
| 20 | 35.25 | 35.25 | 1.2 | 0.9 | 25.0[1] | 2.3[14] | 0.1[10] | 100.0 |
| 21 | 35.25 | 35.25 | 1.2 | 0.5 | 26.1[1] | 1.8[13] | 0.1[10] | 100.0 |
| 22 | 35.25 | 35.25 | 1.2 | 0.9 | 25.3[1] | 2.0[15] | 0.1[10] | 100.0 |
| 23 | 35.25 | 35.25 | 1.2 | 0.5 | 25.7[1] | 2.0[15] | 0.1[10] | 100.0 |
| 24 | 35.25 | 35.25 | 1.2 | 0.9 | 25.5[1] | 1.8[16] | 0.1[10] | 100.0 |
| 25 | 35.25 | 35.25 | 1.2 | 1.3 | 25.1[1] | 1.8[13] | 0.1[10] | 100.0 |
| 26 | 35.25 | 35.25 | 1.2 | 0.9 | 25.1[1] | 2.2[17] | 0.1[10] | 100.0 |
| 27 | 40.25 | 40.25 | 1.2 | 0.9 | 17.4[3] | — | — | 100.0 |
| 28 | 40.25 | 40.25 | 1.2 | 0.9 | 17.4[4] | — | — | 100.0 |

[1]Propylene glycol;
[2]Adipic acid:succinic acid 1:1;
[3]Distilled water;
[4]Glycerine;
[5]Edetate disodium:citric acid 1:1;
[6]Polyethylene glycol 300;
[7]Bis(phenylethynyl)-anthracene;
[8]Edetate disodium:adipic acid:succinic acid 0.8:1:1;
[9]Edetate disodium:adipic acid:succinic acid 1:1:1;
[10]Perylene;
[11]Edetate disodium:adipic acid:succinic acid 1.6:1:1;
[12]Edetate disodium:citric acid 1:1;
[13]Edetate disodium;
[14]Edetate disodium:adipic acid:succinic acid:citric acid 1:6:1:1:1;
[15]Edetate disodium:EDTA 1:1;
[16]Citric acid:EDTA 0.8:1;
[17]Edetate disodioum:citric acid 1.75:1.

Of the foregoing, Example Nos. 2, 3, 5–7, 27 and 28 were prepared without using any stabilizer and without any bleaching agent activator. Upon measuring the concentration of active hydrogen peroxide over time, it was found that the hydrogen peroxide in these examples was not as stable as those formed with a stabilizer. The rate of decomposition was observed to increase as the concentration of hydrogen peroxide increased. This increased decomposition rate demonstrates the importance of the bleaching agent stabilizer in the event that a stable, one-part, pre-mixed bleaching composition is desired, particularly at higher concentrations of peroxide. These stabilizer-less compositions were also slow to react when irradiated with radiant energy and/or UV light from a standard dental curing light since they included no bleaching agent activator. Hence, in those cases where accelerated bleaching is desired, as opposed to slower but more steady bleaching, it is important to include the bleaching agent activator.

Of the foregoing examples set forth in Table 1, Example Nos. 1, 8–11, and 13–14 were made without any bleaching agent activator but did include a stabilizer, or a combination of stabilizers, according to the present invention. Upon measuring the concentration of active hydrogen peroxide over time it was found that the concentration of hydrogen peroxide in these examples remained above 90% of the original concentration after 28 days of storage. As in Example Nos. 2, 3, 5–9, 27 and 28, these compositions were slow to become activated when irradiated with visible and/or UV light using a commercial dental curing light. However, upon irradiating the compositions with heat energy using a heat lamp that emitted in the infrared range, accelerated decomposition of bleaching compositions within about 1 minute was observed.

Of the foregoing examples set forth in Table 1, Example Nos. 4, 12 and 15–26 were made to contain both a stabilizer and a bleaching agent activator according to the present invention. Upon measuring the concentration of active hydrogen peroxide over time it was found that the concentration of hydrogen peroxide in these examples remained above about 90% of the original concentration after 28 days of storage. Upon measuring the concentration of activator over time it was found that the concentration of the bleaching agent activator color remained virtually unchanged after 28 days of storage at an appropriate temperature, e.g. 4° C. Upon irradiating these compositions with visible and/or UV light using a commercial dental curing light, the compositions became activated. Because the concentration of activator remained stable over time, the slight drop in apparent stability of the hydrogen peroxide compared to compositions in which no activator was used was apparently due to the fact that the compositions were not prepared or stored in total darkness.

Although the use of a heat lamp caused the bleaching compositions to become activated, it is not particularly feasible to place a heat lamp near or inside a patient's mouth. Doing so might cause discomfort or injury. On the other hand, the use of visible and/or UV emitting lamps caused little if any discomfort since the heat that was generated was limited to within the bleaching composition as a result of the radiant-energy absorbing substance activator, and even that heat was mild compared to the heat generated by a heat lamp.

In order to more fully teach the invention, the following hypothetical examples are presented. While the compositions of the following examples were not actually physically mixed together, they were derived or extrapolated from actual mix designs and are based on the results determined by observing the behaviors of actual mix designs.

Examples 29–42 are made according to the mixing sequence set forth above for Example 4, except that the identities and concentrations of the various components are altered as set forth in Table 2 below.

TABLE 2

| Example | Active $H_2O_2$ | Water | Thickener | NaOH | Carrier | Stabilizer | Activator | Total |
|---|---|---|---|---|---|---|---|---|
| 29 | 1.1 | 0.1 | 1.2 | 0.2 | 97.3 | $1.0^2$ | $0.1^{10}$ | 100.0 |
| 30 | 3.5 | 3.5 | 1.2 | 0.8 | $90.0^1$ | $1.0^2$ | — | 100.0 |
| 31 | 10 | 10 | 1.2 | 0.8 | $76.9^1$ | $1.0^2$ | $0.1^{10}$ | 100.0 |
| 32 | 20 | 20 | 1.2 | 0.8 | $57.0^1$ | $1.0^2$ | — | 100.0 |
| 33 | 20 | 20 | 1.2 | 0.8 | 56.9 | $1.0^2$ | $0.1^{10}$ | 100.0 |
| 34 | 25 | 25 | 1.2 | 0.8 | 47.0 | $1.0^2$ | — | 100.0 |
| 35 | 25 | 25 | 1.2 | 0.8 | 46.9 | $1.0^2$ | $0.1^{10}$ | 100.0 |
| 36 | 40.25 | 40.25 | 1.2 | 0.9 | $16.0^1$ | $1.3^2$ | $0.1^{10}$ | 100.0 |
| 37 | 50.0 | 33.4 | 1.2 | 0.9 | $11.6^1$ | $2.8^2$ | $0.1^{10}$ | 100.0 |
| 38 | 55.0 | 29.9 | 1.2 | 1.2 | $9.5^1$ | 3.1 | $0.1^{10}$ | 100.0 |
| 39 | 60.0 | 26.4 | 1.2 | 1.3 | $7.6^1$ | 3.4 | $0.1^{10}$ | 100.0 |
| 40 | 70.0 | 19.4 | 1.2 | 1.6 | $19.6^1$ | 3.9 | $0.1^{10}$ | 100.0 |
| 41 | 80.0 | 12.4 | 1.2 | 1.8 | — | 4.5 | $0.1^{10}$ | 100.0 |
| 42 | 90.0 | 1.9 | 1.2 | 1.8 | — | 5.0 | $0.1^{10}$ | 100.0 |

[1]Propylene glycol;
[2]Adipic acid:succinic acid 1:1;
[10]Perylene.

Of the foregoing compositions, Example Nos. 29, 32, 34 and 36–42 include both a stabilizer and a bleaching agent activator according to the present invention. The hydrogen peroxide concentration in these examples remains at a level of at least about 80% of the original concentration after 28 days of storage, while the bleaching agent activator color remains virtually unchanged after 28 days of storage. When irradiated, each of the compositions in these examples is activated.

The present invention may be embodied in other specific forms without departing from its spirit or essential characteristics. The described embodiments are to be considered in all respects only as illustrated and not restrictive. The scope of the invention is, therefore, indicated by the appended claims and their combination in whole or in part rather than by the foregoing description. All changes that come within the meaning and range of equivalency of the claims are to be embraced within their scope.

What is claimed and desired to be secured by United States Letters Patent is:

1. A light or heat activated dental bleaching composition for bleaching a person's teeth comprising:

at least one dental bleaching agent that provides accelerated bleaching activity upon heating the dental bleaching composition;

at least one dye that is not entirely bleached by the dental bleaching agent prior to use of the dental bleaching composition and which, when exposed to radiant energy from a radiant energy source, absorbs at least a portion of said radiant energy and causes the dental bleaching composition to heat up and thereby accelerate bleaching activity of the dental bleaching agent; and a carrier into which the dental bleaching agent and dye are dispersed, the carrier comprising at least one polyol, wherein the dental bleaching agent provides available hydrogen peroxide having a concentration in a range from about 10% to about 80% by weight of the dental bleaching composition when initially mixed with the dye.

2. A light or heat activated dental bleaching composition as defined in claim 1, wherein the dental bleaching agent comprises at least one of aqueous hydrogen peroxide or carbamide peroxide.

3. A light or heat activated dental bleaching composition as defined in claim 1, wherein the dental bleaching agent comprises sodium perborate.

4. A light or heat activated dental bleaching composition as defined in claim 1, wherein the dental bleaching agent provides available hydrogen peroxide having a concentration in a range from about 20% to about 60% by weight of the dental bleaching composition when initially mixed with the dye.

5. A light or heat activated dental bleaching composition as defined in claim 1, wherein the dye comprises an organic dye that is a substantially conjugated hydrocarbon.

6. A light or heat activated dental bleaching composition as defined in claim 5, wherein the organic dye is selected from the group consisting of naphtha-based compounds, anthracene-based compounds, mixtures thereof, and derivatives thereof.

7. A light or heat activated dental bleaching composition as defined in claim 6, wherein the organic dye is selected from the group consisting of 9,10-bis(phenylethynyl)-anthracene, naptho (2,3-a) pyrene, trans-4,4'-diphenylstilbene, 9,1 0-diphenylanthracene, 5,12-bis (phenyethynyl)-napthacene, perylene, coronene, fluoranthene, mixtures thereof, and derivatives thereof.

8. A light or heat activated dental bleaching composition as defined in claim 6, wherein the organic dye is selected from the group consisting of carotenoids, bixin, lycoxanthin, lycophil, canthaxanthin, capsanthin, cryptoxanthin, isomers of carotene, lycopene, mixtures thereof, and derivatives thereof.

9. A light or heat activated dental bleaching composition as defined in claim 1, further comprising radiant energy absorbable particles.

10. A light or heat activated dental bleaching composition as defined in claim 1, wherein the carrier includes a thickening agent.

11. A light or heat activated dental bleaching composition as defined in claim 10, wherein the thickening agent is selected from the group consisting of polyacrylic acid polymers, silicates, and mixtures thereof.

12. A light or heat activated dental bleaching composition as defined in claim 1, wherein the carrier includes at least one of water, polypropylene glycol, polyethylene glycol, sorbitol, propylene glycol, glycerol, steryl alcohol, or a large molecular weight polyol.

13. A light or heat activated dental bleaching composition as defined in claim 1, further including a base.

14. A light or heat activated dental bleaching composition as defined in claim 13, wherein the base is included in an amount so that the dental bleaching composition has a pH in a range from about 2 to about 9.

15. A light or heat activated dental bleaching composition as defined in claim 13, wherein the base is included in an amount so that the dental bleaching composition has a pH in a range from about 3 to about 7.

16. A light or heat activated dental bleaching composition as defined in claim 1, further including a bleaching agent stabilizer.

17. A light or heat activated dental bleaching composition as defined in claim 1, wherein the bleaching composition is a stable, one-part composition that maintains a substantial portion of its original bleaching strength after the bleaching agent and the dye are mixed together but prior to exposing the dye to radiant energy.

18. A light or heat activated dental bleaching composition as defined in claim 1, wherein the bleaching agent maintains at least about 90% of its original concentration one month after the bleaching agent and dye are mixed together.

19. A light or heat activated dental bleaching composition as defined in claim 1, wherein the dye maintains at least about 90% of its original concentration one month after the bleaching agent and dye are mixed together.

20. A light or heat activated dental bleaching composition for bleaching a person's teeth comprising:
   a carrier comprising at least one of water or a polyol;
   at least one dental bleaching agent that provides accelerated bleaching activity upon heating the dental bleaching composition; and
   at least one dye that is not entirely bleached by the dental bleaching agent prior to use of the dental bleaching composition, selected form the group consisting of carotenoids; bixin; lycoxanthin; lycophil; canthaxanthin; capsanthin; cryptoxanthin; isomers of carotene; lycopene; 9,10-bis(phenylethynyl)-anthracene; perylene; naphtho(2,3-a)pyrene; trans-4,4'-diphenylstilbene; 9,10-diphenylanthracene; coronene; 5,12-bis(phenyethynyl)-naphthacene; fluoranthene; naphtha-based compounds; anthracene-based compounds; and mixtures thereof,
   wherein the dental bleaching composition has a pH of at least about 2 and less than 9.

21. A light or heat activated dental bleaching composition for bleaching a person's teeth comprising:
   a carrier comprising at least one of water or a polyol;
   at least one dental bleaching agent that provides accelerated bleaching activity upon heating the dental bleaching composition; and
   at least one dye selected from the group consisting of 9,10-bis(phenylethynyl)-anthracene, perylene, isomers of carotene, and mixtures thereof.

22. A light or heat activated dental bleaching composition for bleaching a person's teeth comprising:
   at least one dental bleaching agent that provides accelerated bleaching activity upon heating the dental bleaching composition; and
   at least one dye that is not entirely bleached by the dental bleaching agent prior to use of the dental bleaching composition and which, when exposed to radiant energy from a radiant energy source, absorbs at least a portion of said radiant energy and causes the dental bleaching composition to heat up and thereby accelerate bleaching activity of the dental bleaching agent; and
   a carrier into which the dental bleaching agent and dye are dispersed, the carrier comprising (i) at least one of water or a polyol and (ii) at least one of a polyacrylic acid polymer or a polyacrylic acid copolymer as a thickener,
   wherein the dental bleaching agent provides available hydrogen peroxide having a concentration in a range from about 10% to about 80% by weight of the dental bleaching composition when initially mixed with the dye.

23. A light or heat activated dental bleaching composition as defined in claim 22, wherein the thickener includes PEMULEN.

24. A light or heat activated dental bleaching composition for bleaching a person's teeth comprising:
   at least one dental bleaching agent that provides accelerated bleaching activity upon heating the dental bleaching composition; and
   at least one dye that is not entirely bleached by the dental bleaching agent prior to use of the dental bleaching composition and which, when exposed to radiant energy from a radiant energy source, absorbs at least a portion of said radiant energy and causes the dental bleaching composition to heat up and thereby accelerate bleaching activity of the dental bleaching agent; and
   a carrier into which the dental bleaching agent and dye are dispersed, the carrier comprising (i) at least one of water or a polyol and (ii) at least one of edetate disodium, EDTA, oxine EDTA, calcium disodium EDTA, adipic acid, succinic acid, citric acid, tin nitrate, tin phosphate, salts of the foregoing, and mixtures thereof.

25. A light or heat activated dental bleaching composition for bleaching a person's teeth comprising:
   a carrier comprising at least one of water or a polyol;
   at least one dental bleaching agent that provides accelerated bleaching activity upon heating the dental bleaching composition; and
   at least one dye selected form the group consisting of bixin; lycoxanthin; lycophil; canthaxanthin; capsanthin; cryptoxanthin; isomers of carotene; lycopene; 9,10-bis(phenylethynyl)-anthracene; perylene; naphtho(2,3-a)pyrene; trans-4,4'-diphenylstilbene; 9,10-diphenylanthracene; coronene; 5,12-bis(phenyethynyl)-naphthacene; fluoranthene; naphtha-based compounds; anthracene-based compounds; and mixtures thereof.

* * * * *

UNITED STATES PATENT AND TRADEMARK OFFICE
CERTIFICATE OF CORRECTION

PATENT NO.    : 6,387,353 B1  
DATED         : May 14, 2002  
INVENTOR(S)   : Steven D. Jensen and Dan E. Fischer Page 1 of 1

It is certified that error appears in the above-identified patent and that said Letters Patent is hereby corrected as shown below:

<u>Column 1,</u>  
Line 50, after "are available as" change "'GLYOXIDES®'" to -- "GLYOXIDE®" --

<u>Column 6,</u>  
Line 44, after "as" change "PEMULEN" to -- PEMULEN® --

<u>Column 8,</u>  
Line 43, before "colorants for" change "a" to -- as --

Signed and Sealed this

Seventeenth Day of September, 2002

*Attest:*

JAMES E. ROGAN  
*Attesting Officer*           *Director of the United States Patent and Trademark Office*